United States Patent [19]

Maslaney et al.

[11] Patent Number: 4,726,676
[45] Date of Patent: Feb. 23, 1988

[54] OPTICAL SIGNAL POWER MEASUREMENT METHOD AND APPARATUS

[75] Inventors: Michael J. Maslaney, Atlanta; Dinal S. Andreasen, Marretta; Clifford D. Brown, Atlanta, all of Ga.

[73] Assignee: General Signal Corporation, Stamford, Conn.

[21] Appl. No.: 826,616

[22] Filed: Feb. 6, 1986

[51] Int. Cl.[4] .................... G01N 21/84; G01N 21/59
[52] U.S. Cl. .................................................. 356/73.1
[58] Field of Search .......................................... 356/73.1

[56] References Cited

U.S. PATENT DOCUMENTS

| | | | |
|---|---|---|---|
| 4,234,253 | 11/1980 | Higginbotham et al. | 356/73.1 |
| 4,257,707 | 3/1981 | Liertz et al. | 356/73.1 |
| 4,280,765 | 7/1981 | Pophillat et al. | 356/73.1 |
| 4,309,105 | 1/1982 | Lebduska | 356/73.1 |
| 4,356,448 | 10/1982 | Brogardh et al. | 250/231 R X |
| 4,645,343 | 2/1987 | Stockdale et al. | 356/326 |

OTHER PUBLICATIONS

Auffret et al, "Field Measurement Set for Attenuation & Bandwidth of Optical Links", Electronics Letters (Oct. 9, 1980), vol. 16, #21, pp. 798–799.

"Optical Fibre Transfer Function Measurement", 9/22/81, A. A. Naoom, Q. V. Davis.
"Simultaneous Measurement of Mode Conversion...", 10-1-81, K. Nagano, A. Ochi, S. Kawakami.
"Method 6010-Radiant Power Measurements", PO-D-STD-1678, 11-30-77.

Primary Examiner—Vincent P. McGraw
Attorney, Agent, or Firm—Barnes & Thornburg

[57] ABSTRACT

An apparatus and method for measuring power and power losses of light transmissions in fiber optic cables. The apparatus includes a tester having a transmitter and a receiver, wherein the transmitter provides at one end of a fiber optical cable a test signal of a known wavelength of light modulated at a known or signature AC frequency. The receiver detects the transmitted signal at a second end of the cable, determines the modulating frequency of the transmitted signal for identifying the transmitted wavelength of light and measures power of the AC signal. If measuring the power loss, the receiver further compares the power intensities of the transmitted signal with the power intensity of a stored reference for determining the power loss associated with the transmission of a known wavelength of light.

28 Claims, 3 Drawing Figures

OPTICAL SIGNAL POWER MEASUREMENT METHOD AND APPARATUS

BACKGROUND AND SUMMARY OF THE INVENTION

The present invention relates generally to an apparatus and method for measuring power and power losses of light transmissions in fiber optic cables, and more specifically, the power and power losses resulting from the transmissions of known wavelengths of light.

Fiber optic cables have been finding increased applications in a variety of industries as a result of their lightweight composition and effectiveness in transferring information. The use of fiber optic cables has, for instance, become common in the telecommunications industry, where many of the bulkier and less efficient wire data lines are being replaced with fiber optic cables. To assure accuracy of the data transmitted by light signals, however, these fiber optic cables are tested by measuring the power losses associated with the light transmissions, and thus, determine the potential error in the data transmissions.

Light signals constituting data transmissions are transmitted through fiber optic cables using specific nominal wavelengths of light for the transmission. Because different wavelengths of light have varying attenuating characteristics, it is important to determine the attenuation of the fiber optic cable with respect to the specific wavelength of light which will be used for the particular data transmission.

In U.S. Pat. No. 4,234,253 to Higginbotham et al., an attenuation measuring system is described as having a transmitter and receiver which are operatively connected to opposite ends of a fiber optic cable under test. A reference signal comprised of a timing pulse is superimposed upon a square wave pulse. This modified square wave signal is then transmitted through the fiber optic cable where it is detected by a receiver attached to a second end of the cable. The receiver separates the timing pulse from the transmitted pulse for use in demodulating the transmitted signal and compares the demodulated square wave signal to a reference signal contained within the receiver. The use of a modified square wave pulse as a test signal, however, has the disadvantages of signal noise and limited bandwidth which are characteristic of DC signals.

U.S. Pat. No. 4,280,765 to Pophillat et al. describes a measuring system for measuring the transmission bandwidth of the fiber optic cable using a plurality of sinusoidal test signals as opposed to square wave pulses. Pophillat, therefore, avoids some of the disadvantages of Higginbotham. This system comprises a frequency generator for producing a first composite signal having discrete distribution of predetermined sinusoidal frequencies. A single laser is provided by which the first composite signal modulates the light signal for transmission through the optical fiber under test. An optical detector is positioned at a receiving end for converting the light signal into a second composite signal and directing the same to a spectrum analyzer. The analyzer provides a frequency spectrum display of the composite of the electrical sinusoidal signals which is compared with the spectrum of the first signal for determining the power attenuation of the first composite of signal transmissions. While the prior art has concentrated on techniques of measuring the response to the specific wavelength of light that is being transmitted, they have failed to address the problem of providing a tester which is capable of being adapted for the varying numbers of wavelengths which may be used. As more and more different sources of light become available, and the quality of light fibers increases, a single tester at a single wavelength will not be sufficient.

It is, therefore, an object of the present invention to provide a means for determining the power losses associated with any specific wavelengths of light transmissions.

Another object of the present invention is to provide a means for identifying the wavelength of light signals transmitted through a fiber optic cable under test and for determining the power losses associated with the respective light wavelengths.

Yet another object of the present invention is to provide a means for determining the power losses associated with specific wavelengths of light transmissions, using either a laser or an LED as a source for the light transmissions.

Still another object of the present invention is to provide a means for measuring the optical power transmitted through a fiber optic cable.

A further object of the present invention is to provide a microprocessor control tester for measuring the power attenuation at each specific wavelength of light transmissions in fiber optics.

These and other objects are attained by providing a transmitter for modulating the power intensities of known wavelengths of light with identifying or signature AC signals. The modulated light is transmitted through a length of fiber under test where the modulated light is then detected and the signature identified by a receiver. The transmitted AC signal is compared with a reference signal stored in a microprocessor for the specific signature to determine the power attenuation of the transmitted signal, thereby determining the transfer characteristics of the fiber optic cable as a function of light wavelengths. By using AC signals to modulate the light wavelength, the problem of noise and limited bandwidth associated with DC signal transmissions are avoided. Nevertheless, a specially preferred embodiment of the tester also includes the capabilities of also measuring the DC power of the transmitted signal.

A specially preferred embodiment of the tester is designed as a modular system, and thus, may be operated as either a single unit (local mode) or a plurality of separate units (remote mode). For fiber optic cables of relatively short length, a single tester unit having both a transmitter module and a receiver module is used, such that the single tester unit attaches to both ends of the cable under test. For cables of longer length, separate tester units having respective transmitting and receiving modules contained therein are provided, whereby the receiver unit includes independently calibrated reference signals for comparison with the received transmitted signal.

Preferred embodiments of the transmitting part of the tester in both single and separate tester operations may include a plurality of laser or light emitting diode (LED) source modules, each module designed to produce a predetermined known mean wavelength of light. Because fiber optic cables do not attenuate the power intensities of different wavelengths of light uniformly, a more accurate representation of the fiber optic cable transmission characteristics results with the use of a plurality of light sources. Each laser or LED source module has assigned to it a modulating AC signal of a specified frequency. After transmission of a nominal wavelength of light modulated on the assigned known frequency, the microprocessor controlled receiver module identifies the modulating frequency for determining which wavelength of light was transmitted, and thereby associate the power loss measurement with the transmitted wavelength of light.

In specially preferred embodiments with a laser light source, the transmitter includes a photodetector for providing input to two feedback circuits, which provide stabilization of the test signal amplitude and wavelength. These feedback loops stabilize the average power or DC level of the light source and maintains the percentage modulation constant. A third feedback which is utilized when the light source is either an LED or a laser, includes a temperature compensation circuit for maintaining the ambient temperature surrounding the light source at a selected temperature. This assures that the light source will have as consistent output as possible. Thus, the feedback circuits assure that during testing, the microprocessor controlled drive units of the respective light sources provide a proper modulation of the assigned wavelength of light.

A unique temperature compensating circuit for a light source is provided. This includes a heater/cooler in a four switch bridge which determines the direction of current through the heater/cooler as a function of temperature variations and, thus, the heating or cooling cycle of the heater/cooler.

Other objects, advantages and novel features of the present invention will become apparent from the following detailed description of the invention when considered in conjunction with the accompanying drawings.

DETAILED DESCRIPTION OF THE DRAWINGS

Figure 1:
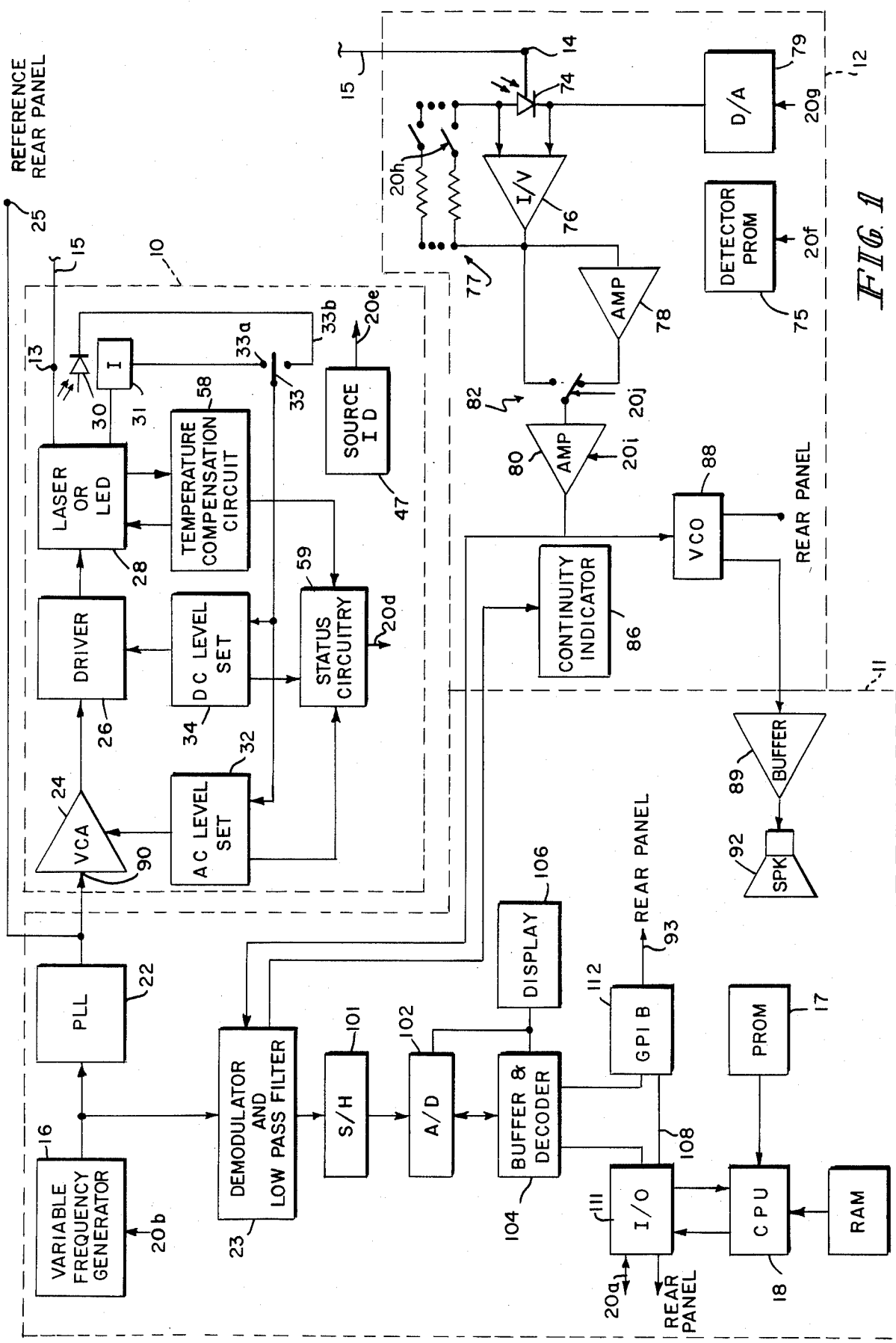
FIG. 1 is a schematic diagram of the tester unit according to a preferred embodiment of the present invention.

Referring to FIG. 1, a modular test unit includes a main frame unit 11, a source module 10 and a detector module 12. An optical cable 15 is connected to source module 10 at 13 and to detector module 12 at 14. The main frame test unit 11 includes a microprocessor 18, a frequency generating circuitry for providing a modulating frequency for the source module 10, and an identifying and demodulating circuitry for identifying the modulating frequency of the signal received by the detector module 12, and demodulating the signal for further processing for input into the microprocessor 18. Each main frame unit 11 includes a microprocessor 18 for controlling the various analog circuits, for storing calibration parameters and for determining the power loss of a transmitted light wavelength signal. The analog circuitry of the main frame unit 11, the detector module 12, and source module 10, are interfaced through an I/O board 111 to the microprocessor 18.

The source module 10 includes a light source 28 having a known center wavelength of light output. The source module 10 receives a specified modulation frequency from the mainframe unit for providing signature modulation, e.g. modulating a known wavelength of light by a known modulating frequency. Each source module is assigned a different modulating frequency, depending upon its wavelength, its type of source, e.g. laser or LED and the calibrated output power. This modulating frequency assignment is stored in each tester's microprocessor's memory 17. In order to insure accuracy of testing by simulating normal operational conditions for fiber optic cable systems which use either laser or LED light sources for their data transmissions, source modules 10 are available which include LED light sources or laser light sources.

The detector module 12 includes microprocessor controlled circuitry for detecting the modulated light signal of a specific wavelength and amplifying the same for receipt by the demodulator circuitry 23 in the main frame unit 11. Because the detector modules 12 each have their own varying responses to different wavelengths of light received, each module 12 is calibrated at the factory for determining this response, which response is stored in the respective PROM's 75 located in the detector module 12. Upon the demodulator 23 in the main frame unit 11 determining the modulating frequency received by the detector module, the microprocessor 18 will match the frequency with its assigned wavelength of light. The microprocessor 18 will then retrieve from the detector module PROM 75 the corresponding calibrated parameters associated with the detector's responsiveness to the light wave received, and will use these parameters in any calculations the microprocessor will perform regarding the received signal.

The tester unit is capable of measuring the optical power of the transmitted light signal received at a second position, or it can determine the power loss of a transmitted light wavelength signal by comparing the power level of the received signal with the power level of a reference signal. The comparison of signals is performed by the microprocessor 18 with the reference signal having been stored in the microprocessor's memory.

By flipping a switch (not shown) on the front panel of the main frame unit 11, the operator may choose between a relative or absolute mode for determining the power loss measurement. In the relative mode, the tester is set up to make a power measurement of any received signal and use this measurement as a relative value for comparing with a second received signal. In an absolute mode, the microprocessor uses as a reference signal, stored information regarding the specific light wave which was transmitted. Each tester main frame unit 11 has stored in its memory the power intensities of all available light signal transmissions. Thus, upon the demodulator circuitry 23 identifying the modulating frequency, the microprocessor retrieves from its memory the reference signal corresponding to the transmitted light wavelength signal and uses the same for determining the received light wavelength signal's power loss.

In a preferred embodiment, the source module 10 transmits an AC signal having a DC bias. The tester system provides the ability to measure the DC optical power by filtering out the AC components, or it can measure the peak AC power of the received signal for determining the power loss associated with the same.

By attaching or removing different source and detector modules, the configuration of the test system can be changed. By including both source 10 and detector 14 modules in a signal test unit, the tester is set up in a local mode, whereby the tester provides a test signal at the source module output 28 to a first end 13 of a fiber optic cable 15 and detects the transmitted signal at a second end 14 of the fiber optic cable 15 by an input to the detector module 74.

If the fiber optic cable 15 under test is too long for local or single tester applicability, a second main frame unit (not shown) will be required at the second end of the fiber optic cable 15 under test. In this remote mode of testing, the first main frame unit 11 with a source module 10 can be set up to transmit the test signal to the first end 13 of the cable 15. The second main frame unit (not shown) is set up as the receiver requiring only a receiver module 12 for detecting and measuring the power of the received wavelength test signal. The second main frame uses its microprocessor to identify the signature of the transmitted signal and provides the appropriate controls and reference signal for the detector module. If source 10 and detector 12 modules are duplicated in both main frame units, the test signal may be sent in either direction of the cable length, thereby providing a testing system having bi-directional test capabilities.

The modularity of the testing system also allows for the interchangability of different source modules 10, having different wavelength test signals. This allows for a flexibility in testing any number of available wavelengths by merely interchanging the source module 10. Each detector module 12 is calibrated at the factory for responding to all available light sources. A modulating AC signal is generated by a microprocessor controlled frequency generator 16 located in the main frame 11 of the tester unit. The frequency of the modulating AC signal is controlled by data signals received from the microprocessor 18 through I/O ports 20a and 20b of the microprocessor 18 and generator 16 respectively. In the preferred embodiment shown, the frequency generator 16 provides a nominal output frequency of 10 KHz. The output of the frequency generator 16 is provided to an input of a phase lock loop (PLL) 22 having a voltage control oscillator (VCO), as well as to an input to a demodulator and low pass filter 23. The output of the PLL 22 provides an AC signal of a known frequency to the input of a voltage control amplifier (VCA) 24 which serves as the input to the source module 10. The VCA in turn provides an AC signal of a specified average voltage to a driver circuit 26. The output of the PLL 22 is also provided at a terminal 25 on the rear panel of the main frame unit 11 for referencing the AC signal. The driver circuit 26 then provides a light source 28 with a nominal bias current having frequency corresponding to the frequency of the AC signal provided by the frequency generator 16, an average AC power determined by the VCA 24 and a DC bias level determined by the driver circuit 26. The light source 28 comprising either a laser or light emitting diode (LED), then provides a modulated light signal of a known wavelength modulating frequency and power level to the fiber optic cable 13.

The output of the light source 28 is provided as a feedback circuit to control the light source. If a laser source is used, a photodetector 30 senses the output of the laser and provides it on line 33b to switch 33 which is connected during assembly of the source module. If a LED is used as a source, a current measuring circuit 31 is provided and connected to line 30a. The selected feedback signal is provided to the AC level set circuit 32 which should adjust the gain of the VCA 24 and to DC level set 34 to adjust the driver circuit 26. A temperature compensation circuit 58 is also provided to control the temperature of either laser or LED sources 28. Status circuitry 59 is connected to the temperature compensation circuit 58, the DC level circuit 34 and the AC level circuit 32 to provide a visual indication of the proper operating status of this system as well as communicating the status to the CPU via I/O port 20d.

A source identification circuit 47 is included in every source module 10 to identify to the main frame tester unit 11 the type of light source the particular source module 10 represents via I/O port 20e. The microprocessor 18, can therefore, retrieve from its memory, the necessary data for programming the respective components of the source module 10 via I/O ports 20.

Figure 2:
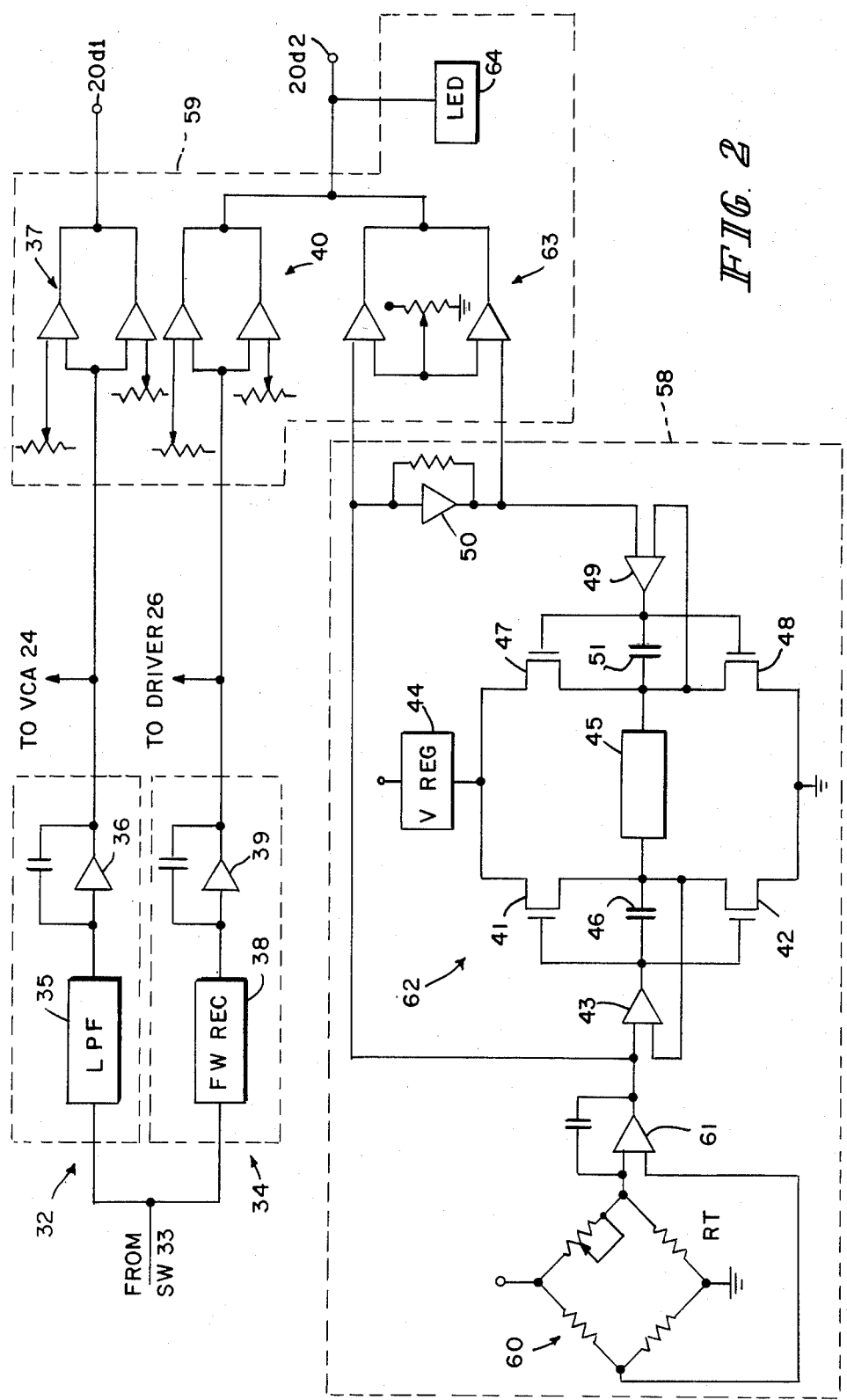
FIG. 2 is a more detailed schematic diagram of the feedback and status circuits as shown in FIG. 1.

The details of the feedback and status circuitry are illustrated specifically in FIG. 2. The DC level set circuit 32 includes a low pass filter 35 and an integrator 36. Their output is provided to a window detector 37 in the status circuitry 59. If the signal is within the high and low value determined by the window detector 37, a positive indication is given on terminal 20d1 to the CPU. The AC level set circuit 34 includes a full wave rectifier 38 and an integrator 39 providing a signal to window detector 40 of the status control circuitry 59. If this value is within the high and low limits set by the window detector, it will provide a positive output on terminal 20d2 to the I/O port. The visual indication in LED 64 is connected to the terminal 20d2 and is lit if the DC level is within the acceptable limits.

The temperature compensation circuit 58 is included in the source module 10 when a laser or LED source is used, for maintaining a preselected temperature surrounding the laser or LED source 28. In the preferred embodiment, a temperature of approximately 25° C. is maintained about the light source. The compensation circuit 58 includes a resistive bridge 60 including a thermistor RT. An integrator 61 connected across the output of resistor bridge 60 provides an input to the control circuit 62 for peltier 45 for heating or cooling the light source and an input to window comparator 63 of the status circuitry 59. The control circuitry 62 for the peltier 45 is constructed as a current switching bridge including serially connected P-channel transistor 41 and N-channel transistor 42 in parallel with series connected P-channel transistor 47 and N-channel transistor 48 between a current limiter and ground. The peltier device 45 is connected between the two parallel legs. The output from the integrator 61 is provided as an input to the gates of the transistor pairs 41 and 42 via amplifier 43. The signals on the drain of the transistor pairs are provided as a second input to the amplifier 43. A capacitor 46 is connected between the gates and sources of the transistors 41 and 42 for providing stability. The output of integrator 50 is connected as an input signal to amplifier 49, and in turn, the output of amplifier 49 is connected to the gates of transistor pair 47 and 48. The sources of the transistor pair 47 and 48 are also connected as a second input to the amplifier 49. A capacitor 51 is connected between the common gates and sources of the transistor pair 47 and 48 for providing stability. Depending upon the high or low value of the output signal sensed by the resistor bridge 60, diagonally opposing transistors of the control circuit will be activated to control the degree and direction of current through the peltier device. For current in one direction, the peltier device will heat up and for current in the other direction, it will cool. By way of example, if a positive signal is provided on amplifier 43, the N-channel device 42 will be on and the P-channel device 41 will be off. The inverted signal on amplifier 49 will turn on P-channel device 47 and turn off N-channel device 48. Thus, the current path will be from the voltage regulator 44 through P-channel device 47, laser peltier 45, N-channel device 42 to ground. The low voltage signal at the source of 42 is fed back to amplifier 43 to further increase its differential as will the current signal on the source of transistor 53 be provided to the amplifier 49. For a low input signal, the inverse occurs, namely P-channel 41 and N-channel 48 are on providing a current path through peltier 45 in the opposite direction. The inverted and non-inverted input signals are provided to the window detector 63 which provides an output signal to I/O port 20d2 as well as to the LED 64.

The detector module 12 of the receiving part of the test system includes a photodetector 74 arranged at a second end 14 of the fiber optic cable 15. A detector prom module 75 is included in each detector module 12 for storing information relating to the responsivity of the specific photodetector 74 to different wavelengths of light, also gain, absolute calibration factors, type of detector, and parity checker bits. Because the photodetector 74 will respond differently to different wavelengths of light, the detector 74 is tested during the manufacturing and assembly of the detector module 12 for determining this variance, with the resulting information stored in the detector prom 75. This information is retrieved by the microprocessor 18 via I/O port 20f from the detector prom 75 during the normal testing operation as compensating factors in order to eliminate the responsivity of the photodetector 74 to light wavelengths in determining the power of attenuation of the test signals.

The photodetector 74 provides a current equivalent to the power intensity of the detected transmitted signal to a microprocessor controlled variable gain current-to-voltage I/V converter 76. The microprocessor 18 via D/A converter 79 and I/O ports 20g controls the reference signal for I/V converter 76 and via I/O 20h the gain of resistors 77 by switching different resistors into the feedback of the I/V converter 76. The output of the I/V converter 76 is then supplied either directly to amplifier 80 whose gain is microprocessor controller via I/O 20i or supplied indirectly to the same via amplifier 78, as determined by switch 82 controlled by I/O 20j. The output of amplifier 80 in turn provides the input to a demodulator 84 located in the main frame test unit 11. Additionally, this output is provided to a speaker 92 via serially connected voltage control oscillator 88 and buffers 89. An output of a demodulator 23 in the main frame 11 provides the input to a continuity indicator circuit 86 located in the detector module 12. The indicator 86 includes an LED for indicating the presence of a detected signal by photodetector 74.

The demodulator 23 receives an AC reference signal from the frequency generator 16. In local mode, the transmitter and receiver components are in one unit and, thus, the demodulator 23 merely references the output of the frequency generator 16 to determine the frequency of modulation. In remote mode, the main frame unit which is at the receiving end of the cable, does not have this initial information, and thus, must step the frequency generator 16 through all the possible modulating frequencies of the transmitter which are stored in the microprocessor's memory in the receiving unit, and compare the same with the received signal to determine the AC modulating frequency of the transmitter. The demodulator 23 then receives the necessary frequency components.

The output of the demodulator 23 provides the input to a sample and hold circuit 101 and A/D converter 102. The A/D converter 102 in turn provides the input to a buffer and decoder 104 and to an alphanumeric display 106. The buffer and decoder 104 is further coupled to a data bus 108 which connects to the I/O circuit 111 and General Purpose Interface Bus (GPIB) 112. The I/O circuit 111 is also coupled to the central processing unit (CPU) 18.

Figure 3:
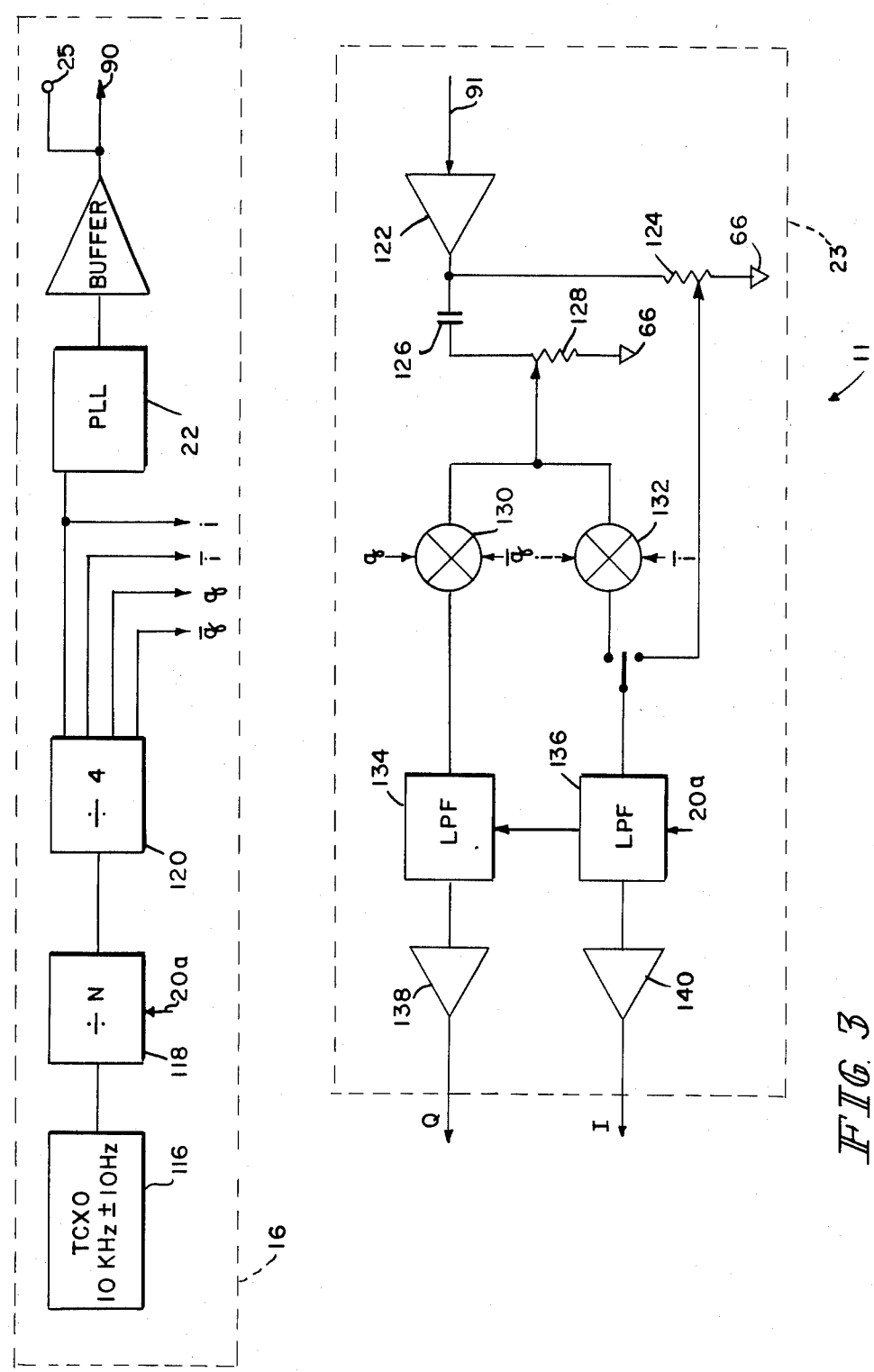
FIG. 3 is a more detailed schematic diagram of the variable frequency generator and demodulator as shown in FIG. 1.

FIG. 3 shows a more detailed schematic diagram of a preferred embodiment of the frequency generator 16 and demodulator 23. The frequency generator 16 includes a temperature compensated crystal oscillator (TCXO) 16 which provides the input, e.g. 10 KHz to a first microprocessor controlled multiple divider 118 having I/O ports 20a connected to the microprocessor 18. In the preferred embodiment, the multiple divider 118 provides assigned frequencies in steps of 40 Hz from the nominal frequency of 10 KHz for assigning a specific AC frequency of modulation to each wavelength of light to identify the wavelength with a signature or identifying AC frequency. The output of the multiple divider 118 is then provided to a divide-by-four divider 120 for providing an output signal to the PLL circuit 22 and frequency components q, $\bar{q}$, i, $\bar{\imath}$ representing the generated frequency to the demodulator 23.

The demodulator 23 includes an amplifier 122 whose output is connected to ground via variable resistance 124 for providing DC gain, and via capacitance 126 and variable resistance 128 for providing AC gain. A circuit for providing the equivalent peak value of the received AC component is connected between the output connections of amplifier 122 and the sample and hold circuits 101. This circuit comprises parallel mixers 130 and 132 having inputs connected to the respective output signals of the divide-by-four divider 120 or to the microprocessor, depending upon the mode the system is operating under. The mixers 130, 132 have a common connection with variable resistance 128 for receiving the received transmitted signal from amplifier 122. The respective outputs of mixers 130, 132 are connected to respective microprocessor controlled low pass filters 134, 136 and to respective amplifiers 138, 140. The output of the amplifiers 138, 140 provide the Q and I components respectively, which are then provided to respective inputs to the sample and hold circuit 101, and A/D converter 102, respectively of FIG. 1.

In the operation of the measuring system, the frequency generator 16 is programmed to produce a specific frequency output. The frequency output of the generator 16 will then be processed through the phase lock loop 22 and further processed by a voltage control amplifier 24 and driver circuit 26. A bias current provided by the driver circuit 26 will modulate the light source 28 at the assigned frequency of the generator's output, and at the power intensity provided by the VCA and driver circuits. The light source 28 comprises either a laser or LED having a known central wavelength associated with its light signal output. The source module 10 includes at least one of these light sources 28 with each of the sources providing a light signal of a distinct central wavelength. The microprocessor 18 programs the frequency generating system 16 to generate a specific frequency to correspond to each of the light sources 28, thereby providing an identification or signature modulation for the particular light wavelength of each source. Because the modules and main frame units are calibrated to a common standard in the loss absolute mode of measurement, further calibration is no longer required of the tester system in the field or in the lab.

A photodetector 30 is arranged near the light source 28 or a current senser 31 for providing a feedback signal to the respective AC and DC level controls, 32, 34. The respective circuits provide for stabilizing the amplitude and frequency of the AC signal by controlling the AC level of the VCA 24 and the DC level of the driver circuit 26. The status circuit 59 receives output signals from the feedback circuits 32, 34, 58 and compares the sum of the output signals for comparing with maximum and minimum parameters provided in each feedback circuit. If the status signal falls outside the limit of the parameters of the comparator circuits, an LED 63 will light up and the microprocessor will provide a message on the display means 106 indicating that the status of the transmitter is out of specification.

Once the modulated light signal is transmitted through the fiber cable 15, the photodetector 74 of the detector module 12 detects the signal at a second end 14 of the fiber cable 15 and converts the light signal into an equivalent current signal. This current signal is then supplied to a microprocessor control current-to-voltage converter 76. The output voltage of the amplifier 76 is directed to microprocessor controlled-amplifiers 78 and 80 which serve as an auto-ranging circuit.

The output of amplifier 80 provides the input to a demodulator 23, and the voltage control oscillator (VCO) 88. The VCO drives a speaker 92 via buffer 89 for aurally indicating the signal strength received at the photodetector 74.

If the apparatus is set up in a local or internal mode e.g. having only a single unit, then the necessary information for determining a frequency of modulation or demodulating the received signal in the modulator 23 is provided directly from the frequency generator 16. If the apparatus is operated in a remote or external mode e.g. having two separate units for the transmitter and receiver, then the receiving unit's microprocessor 18 will step its frequency generator 16 through the various frequency to determine a match and lock it in to provide the necessary signals to the receiving unit demodulator 23.

Upon identifying the modulating frequency, the microprocessor in the receiver main frame unit 11 will provide through respective I/O ports 20a the necessary signals for adjusting the gain of respective current-to-voltage amplifier 76 in the detector module 12. Additionally, the microprocessor 18 will identify from its memory the particular light wavelength assigned to the detected modulating frequency, and thereby incorporate compensating parameters from the detector PROM 75 of the detector module 12 which correspond to the specific photodetector's 74 responsivity to that particular light wavelength.

The demodulation and low pass filter 23 will provide the equivalent peak value of the received modulating signal in the external mode. These values are determined originally during the manufacturing and calibration process of the apparatus system, and stored within the microprocessor's memory for each assigned frequency. The output of the demodulator and low pass filter 23 will then be supplied to a sample and hold 101 and an analog-to-digital converter 102. This information is further processed by the microprocessor 18 by comparing the received values corresponding to the power intensity of the received signal to that of a reference signal stored in the microprocessor 18. This reference signal may be an absolute value determined during the calibration of the system at the assembly plant, or may be a relative value determined by testing a reference cable immediately before the present test for using the result of the reference cable as a relative value. The microprocessor 18 will calculate the difference between the received transmitted signal of known wavelength of light and the reference value for determining the attenuation associated with the transmission of the particular light wavelength. This attenuation will then be displayed on the display means 106 and may be stored within the microprocessor's memory for further analysis. The microprocessor will then start the above procedure over for new wavelengths of light transmitted by a new laser or LED source. Also, through the use of the General Purpose Interface Bus (GPIB), the resulting information may be outputted to a printer or other digital controlled mechanism.

Although certain preferred embodiments provide for modulated light signals having the same power levels prior to transmission, the tester is capable of having varying power levels assigned to the specific modulated light signals.

From the preceding description of the preferred embodiments, it is evident that the objects of the invention are attained, and although the invention has been described and illustrated in detail, it is to be clearly understood that the same is by way of illustration and example only and is not to be taken by way of limitation. The spirit and scope of the invention are to be limited only by the terms of the appended claims.

What is claimed is:

1. A tester for measuring the optical power attenuation of light signals having specific wavelengths and powers transmitted through a fiber optic cable, comprising:

light source means for producing a light signal having a specific wavelength and power level;

modulating means for modulating said light signal with an assigned AC frequency identifying said specific wavelength and power level;

transmitting means for transmitting said modulated light signal at a first point along said fiber optic cable;

receiving means for receiving said modulated signal at a second point along said fiber optic cable;

identifying means for determining the modulating AC frequency of said received modulated signal and providing a reference signal as a function of said specific wavelength and power level identified by said modulating AC frequency; and computing means for comparing said received modulated signal with said reference signal and providing a signal representing the quality of transmission as a function of said comparison.

2. The tester of claim 1, wherein said light source means for producing said light signal includes laser emission means.

3. The tester of claim 1, wherein said transmitting means includes a feedback means for maintaining the temperature at said light emission means in a predetermined range.

4. The tester of claim 1, wherein said light source means for producing said light signal includes a light emitting diode.

5. The tester of claim 4, wherein said transmitting means includes a feedback means for stabilizing the amplitude and frequency of said modulated light signal.

6. The tester of claim 1, wherein said modulating means for modulating said light signal includes a frequency generator means having a known frequency output.

7. The tester of claim 6, wherein said receiving means includes a photodetector means for detecting said modulated signal.

8. The tester of claim 7, further including a display means for indicating said power attenuation.

9. The tester of claim 1, wherein said AC frequency of said modulating means also identifies the type of light source and said identifying means provides a reference signal also as a function of the type of light source identified by said modulating AC frequency.

10. The tester of claim 1, wherein said light source means includes a plurality of light sources for producing a plurality of light signals, each of said light signals having a distinct wavelength wherein said modulating means includes a frequency generator means having a plurality of AC frequencies for modulating each of said light signals with a unique AC frequency identifying the light source and its wavelength.

11. The tester of claim 10, wherein each of said light source has a distinctive combination of wavelength, power level and type of source and AC frequency of said modulating means identifying the type of light source, wavelength and power level.

12. The tester of claim 10, wherein said light source means include a plurality of laser emission means for producing said plurality of light signals.

13. The tester of claim 10, wherein said light source means further includes a plurality of light emitting diodes for producing said plurality of light signals.

14. The tester of claim 11, further including a microprocessor having a memory for storing the plurality of said AC modulation frequencies, wherein said microprocessor identifies the wavelength, power level and type of light source of the transmitted light, upon said identifying means determining the AC modulation frequency.

15. The tester of claim 14, wherein said receiving means includes a continuity indicator means for providing a respective signal indicating the receiving means is receiving said modulated signals.

16. The tester of claim 14, wherein said receiving means includes a means for aurally indicating the signal strength received by said receiving means, wherein said means includes a speaker means and a voltage to frequency converter means for driving said speaker means.

17. The tester of claim 14, wherein the receiving means further includes a memory means having compensating values representative of the varying responsivity of said receiving means to said modulated signals for providing said microprocessor compensating parameters.

18. An apparatus for measuring the power attenuation of light transmissions of a fiber optic cable comprising:
a transmitter means for modulating at least one known wavelength of light with a known AC frequency identifying said wavelength and power intensity, and transmitting said modulated of light at a first point along a fiber optic cable;
a receiving means for detecting the power intensity of and identifying said modulated wavelength of light by its AC frequency of modulation at a second point along said fiber optic cable, wherein said receiving means includes means for providing a unique reference signal having a power intensity for each identifying modulated wavelength as a function of said known wavelength and power intensity identified by said AC frequency and comparing said power intensity of said detected modulated signal with said power intensity of said reference signal.

19. The apparatus of claim 18, further comprising a display means for indicating said power attenuation.

20. The apparatus of claim 19, wherein said transmitter means includes a light source means for generating at least one discrete light signal of a known wavelength and power intensity and a variable frequency generator means for generating a corresponding discrete AC signal of a known frequency.

21. A modulator testing system for measuring optical power of light signals having specific wavelengths and power levels of light transmitted through fiber optic cables, said tester comprising:
a transmitting means including a light source of a nominal wavelength and power level, a driver means for driving said light source and means for identifying said nominal wavelength and power level;
first control means connected to said transmitting means for monitoring said identifying means, and activating said driver means with a signatory AC signal as a function of said nominal wavelength and power level; and
receiving means including a light detector element, means for providing a reference signal as a function of the wavelength and power level identified by the signatory AC signal detected by detector element and means for comparing said reference signal with said detected AC signal.

22. A tester of claim 21, including means for removably connecting said transmitting means to said control means.

23. A tester of claim 21, including means for removably connecting said detector element to said receiving means.

24. A tester of claim 23, wherein said detector element includes means for identifying said detector element and said receiving means includes means for adjusting said comparison means as a function of said identified detector.

25. A tester of claim 21, wherein said receiving means includes means for recognizing said signatory of said detected AC signal.

26. A tester of claim 25, wherein said first control means includes means for providing said signatory AC signal used to activate said driver to said recognizing means for recognizing said signatory of said detected AC signal.

27. A tester of claim 25, wherein said receiving means includes a second control means for providing a plurality of signatory AC signals to said recognizing means for recognizing said signatory of said detected AC signal.

28. The testor of claim 21, wherein said identifying means of said transmitting means also identifies the type of light source, and said reference means provides a reference signal also as a function of said type of light source, said signatory AC signal of said first control means is also a function of the type of light source.

* * * * *